US00PP24705P2

(12) United States Plant Patent
van der Spek

(10) Patent No.: US PP24,705 P2
(45) Date of Patent: Jul. 29, 2014

(54) ***HYDRANGEA* PLANT NAMED 'STMS1'**

(50) Latin Name: *Hydrangea macrophylla×serrata*
Varietal Denomination: STMS1

(75) Inventor: Daan van der Spek, Nootdorp (NL)

(73) Assignee: Flower Time II Inc, Center Moriches, NY (US)

( * ) Notice: Subject to any disclaimer, the term of this patent is extended or adjusted under 35 U.S.C. 154(b) by 160 days.

(21) Appl. No.: 13/506,048

(22) Filed: Mar. 22, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

(56) References Cited

PUBLICATIONS

Midnight Salsa *Hydrangea* retrieved on Oct. 17, 2013, retrieved from the Internet at <http://tess2.uspto.gov/bin/showfield?f=doc&state=4804:lyx3ai.4.3> 2 pp.*
Niemiera Bigleaf *Hydrangea*, Virginia Cooperative Extension 3010-1463, 2010, pp. 1-2.*

* cited by examiner

*Primary Examiner* — June Hwu
(74) *Attorney, Agent, or Firm* — Cassandra Bright

(57) ABSTRACT

A new and distinct *Hydrangea* cultivar named 'STMS1' is disclosed, characterized by a full, round mophead type inflorescence and deep pink petal with a creamy interior coloration and unique serrate petal margins. Plants are characteristically strong and resistant to breaking, and produce dark green foliage. The new variety is a *Hydrangea*, normally used for ornamental indoor or outdoor purposes.

2 Drawing Sheets

Figure 1:
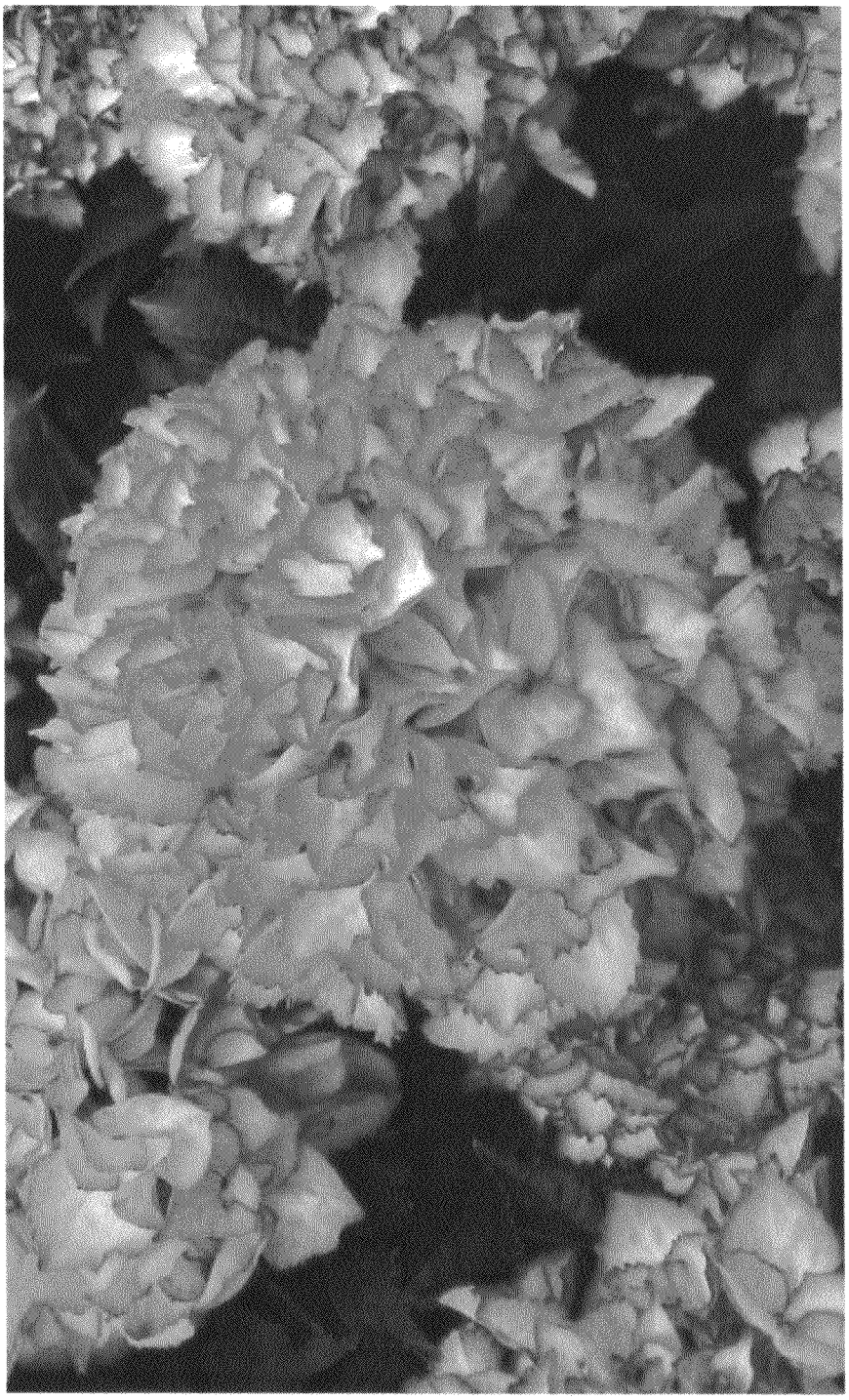

Latin name of the genus and species: *Hydrangea macrophylla×serrata.*

Variety denomination: 'STMS1'.

BACKGROUND OF THE INVENTION

The new cultivar is a product of a planned breeding program. The intent of the breeder program was to develop *Hydrangea* varieties with strong stems and attractive flower colors. The new variety was discovered as seedling within the planned breeding program. This seedling is a result from the crossing of the female parent, an undistributed proprietary variety referred to as 9626 with the male parent, an undistributed proprietary variety referred to as 9659. It was selected by Daniel van der Spek in May of 2002 in Nootdorp, the Netherlands.

Asexual reproduction of the new cultivar 'STMS1' by vegetative cuttings was first performed in Nootdorp, the Netherlands during 2002 and has shown that the unique features of this cultivar are stable and reproduced true to type on successive generations.

Asexual reproduction of the new cultivar 'STMS1' by vegetative cuttings was performed in Nootdorp, the Netherlands and has shown that the unique features of this cultivar are stable and reproduced true to type through 6 successive generations.

SUMMARY OF THE INVENTION

The cultivar 'STMS1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'STMS1' These characteristics in combination distinguish 'STMS1' as a new and distinct *Hydrangea* cultivar:

1. Full, round mophead inflorescence.
2. Unique sepal coloration, creamy interior petal and deep pink margins.
3. Dark green foliage.
4. Strong plant, resisting breaking in production and post-harvest situations.
5. Unique serration to sepal margins.

PARENTAL COMPARISON

Plants of the new cultivar 'STMS1' are similar to plants of the female parent, '9626' in most horticultural characteristics, however, plants of the new cultivar 'STMS1' differ from '9626' in the following characteristics;

1. Flower color of 'STMS1' is white with a deep pink margin whereas '9626' is solid light pink.
2. 'STMS1' has more flowers per inflorescence.
3. 'STMS1' has a wider inflorescence.
4. 'STMS1' is a shorter plant than '9626'.

Plants of the new cultivar 'STMS1' are similar to plants of the male parent, '9659' in most horticultural characteristics, however, plants of the new cultivar 'STMS1' differ from '9659' in the following characteristics;

1. Foliage color of 'STMS1' is darker than '9659'.
2. 'STMS1' is a shorter plant.
3. Flowers of 'STMS1' have a distinctive darker margin whereas '9659' has solid color flowers.

COMMERCIAL COMPARISON

Plants of the new cultivar 'STMS1' are similar to plants of the commercial variety 'Sidaseli', U.S. Plant Pat. No. 20,124 in most horticultural characteristics. However, plants of the new cultivar 'STMS1' differ from 'Sidaseli' in producing an inflorescence that is a round, mophead, compared to the flattened lacecap of 'Sidaseli'. Additionally, 'STMS1' produces flowers with a serrated margin to the sepal.

Plants of the new cultivar 'STMS1' are similar to plants of the commercial variety 'Sidastel', U.S. Plant Pat. No. 20,147 in most horticultural characteristics. However, plants of the new cultivar 'STMS1' differ from 'Sidastel' in producing sepals of a different shade of red-purple. Additionally, 'STMS1' produces flowers with a distinctive serrated margin to the petal not found in 'Sidastel'.

BRIEF DESCRIPTION OF THE PHOTOGRAPHS

The accompanying photograph in FIG. 1 illustrates in full color a typical flower of 'STMS1'.

Figure 2:
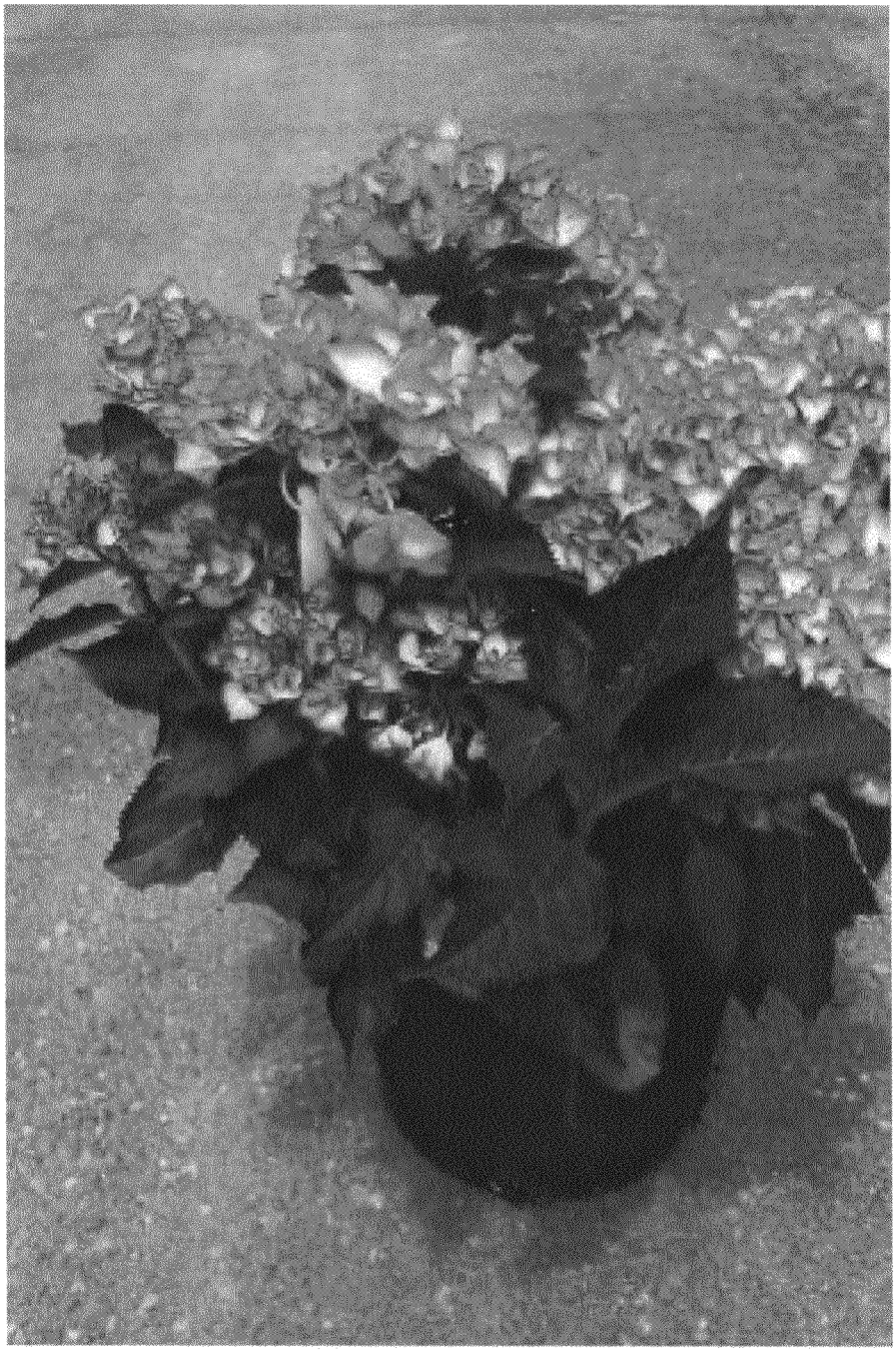

FIG. 2 shows a blooming plant of 'STMS1' grown in a greenhouse. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Mini Chart, 2005 except where general terms of ordinary dictionary significance are used. The following observations and measurements describe 'STMS1' plants grown in a poly house in Mattituck, N.Y., USA from approximately Spring 2010 to Summer 2011. The growing temperature ranged from 4.5° C. to 10° C. at night to 17° C. to 21° C. during the day. Plants have not been allowed to freeze. Measurements and numerical values represent averages of typical flowering types.

Botanical classification: *Hydrangea macrophylla×serrata* 'STMS1'.

PROPAGATION

Time to rooting: 19 to 21 days at approximately 20° C.
Root description: Fine, fibrous.

PLANT

Growth habit: Flowering perennial shrub.
Height: Approximately 45 cm.
Plant spread: Approximately 52 cm.
Growth rate: Moderate.
Branching characteristics: Branches easily from base.
Basal branching: Yes
Length of lateral branches: Approximately 34 cm.
Number of lateral branches: Varies, depending on pinches given to plant. Normally 6 to 8 from 1 or 2 pinches.
Diameter of lateral branches: Approximately 0.7 cm.
Internode length: 4-9 cm.
Lateral branch shape: Round.
Lateral branch strength: Very strong.
Stem color, immature: Near RHS Yellow-Green 145A.
Stem color, mature: Near RHS Yellow-Green 146C
Stem pubescence: No
Other stem or plant characteristics: Stems covered with lenticels at a density of approximately 5.5 lenticels per 1 cm stem length.
*Lenticel length*.—Approximately 0.16 cm.
*Lenticel width*.—Approximately 0.075 cm.
*Lenticel color*.—Near RHS Greyed-Purple 187A.
Number of leaves per lateral branch: Average 8.
Age of plant described: Approximately 1.5 year.

FOLIAGE

Leaf:
*Arrangement*.—Opposite.
*Compound or single*.—Single.
*Average length*.—Approximately 10-12 cm.
*Average width*.—Approximately 6-8 cm.
*Shape of blade*.—Elliptic.
*Apex*.—Acute.
*Base*.—Acute.
*Attachment*.—Stalked.
*Margin*.—Serrate.
*Texture of top surface*.—Glabrous.
*Texture of bottom surface*.—Glabrous.
*Leaf internode length*.—Approximately 6.38 cm.
*Color*.—Young foliage upper side: Near R.H.S. Green 137A, and flushed heavily Greyed-Purple 187A. Amount of flushing varies with light intensity. Young foliage under side: Near R.H.S. Green 137A, and flushed heavily Greyed-Purple 187A. Amount of flushing varies with light intensity. Mature foliage upper side: Near R.H.S. Green 137A, and flushed heavily Greyed-Purple 187A. Amount of flushing varies with light intensity. Mature foliage under side: Near R.H.S. Green 137B, and flushed heavily Greyed-Purple 187A. Amount of flushing varies with light intensity.
*Venation*.—Type: Pinnate. Venation color upper side: Near R.H.S. Yellow-Green 145B. Venation color under side: Near R.H.S. Yellow-Green 145A. Durability of foliage to stresses: High.
*Petiole*.—Average Length: Typically 2-3.5 cm. Diameter: Approximately 0.3 cm. Color: Near R.H.S. Yellow-Green 145A. Texture, upper side: Glabrous. Texture, under side: Glabrous.

FLOWER

Bloom period:
*Blooming period*.—Naturally blooming July through August.
*Blooming in greenhouse production*.—Approximately 90 days from dormant state to blooming.
Inflorescence:
*Arrangement*.—Terminal corymb.
*Commercial type*.—Mophead.
*Panicle height*.—9-15 *cm*.
*Panicle diameter*.—18-25 *cm*.
*Quantity of flowers per inflorescence*.—Fertile flowers, approximately 40. Sterile Flowers, approximately 70-90.
Bud:
*Bud shape fertile flowers*.—Globose with 5 connate petals
*Bud length fertile flowers*.—Approximately 5 mm.
*Bud diameter fertile flowers*.—Approximately 5 mm.
*Bud color fertile flowers*.—Near R.H.S. Purple N77A.
Flower:
*Shape*.—Globose.
*Facing direction*.—Outward.

*Diameter of entire flower*.—Fertile: Approximately 0.5 cm. Sterile: 4-7 cm.
*Depth of flower*.—Fertile: Approximately 0.5 cm. Sterile: 0.5-2 cm.
*Rate of opening*.—Individual flowers: Fully open approximately 4 days from the bud stage.
*Flower longevity on plant*.—Fertile flowers: Approximately 4 weeks. Sterile flowers: Approximately 4 weeks.
*Persistent or self-cleaning*.—Persistent.
*Fragrance*.—No.

Petals.—Fertile flowers only:
*Length of petal*.—Fertile: 0.5 cm.
*Width of petal*.—Fertile: 0.3 cm.
*Apex*.—Acute.
*Shape of petal*.—Connate.
*Petal margin*.—Serrate.
*Petal arrangement*.—Rotate.
*Petal number*.—Average 5.
*Petals fused*.—Yes.
*Petal appearance*.—Matte.
*Petal texture*.—Glabrous top and bottom.

Color:
*Upper surface at first opening*.—Fertile: Near RHS Red 49D with margin Red-Purple 64D.
*Upper surface at maturity*.—Fertile: Near RHS Red-Purple 63A, margin 64D, base near Red 52D.
*Upper surface at fading*.—Fertile: Near RHS Greyed-Orange 165A.
*Under surface at first opening*.—Fertile: Near RHS Red-Purple 64D.
*Under surface at maturity*.—Near RHS Red-Purple 64D.
*Under surface at fading*.—Near RHS Greyed-Orange 165A.

Petaloids: No.
Fragrance: None.

SEPAL

Number:
*Fertile*.—5.
*Sterile*.—4.

Sepal texture: Glabrous.
Sepal arrangement: Rotate.
Sepal length:
*Fertile*.—3 mm.
*Sterile*.—Average 3.75 cm. One sepal is large, 2 are the same size and one is smaller.

Sepal width:
*Fertile*.—2 mm.
*Sterile*.—3.75 cm.

Sepal shape:
*Fertile*.—Elliptic.
*Sterile*.—Reinform with broadly acuminate apex.

Base:
*Fertile*.—Acute.
*Sterile*.—Ovate.

Apex shape:
*Fertile*.—Acute.
*Sterile*.—Broadly acuminate.

Margin:
*Fertile*.—Entire.
*Sterile*.—Serrate.

First opening, sterile color:
*Upper side*.—Near RHS Yellow-White 158B flushed Red-Purple 67A towards margin.
*Under side*.—Near RHS Yellow-White 158B flushed Red-Purple 64A towards margin.

Mature color, sterile: Near RHS 157B at base with a margin of Red-Purple 67A.
*Under side*.—Base RHS White 155B. center flushed Red-Purple 64D with a margin of 67A.

Fading color, sterile:
*Upper side*.—Base near RHS White N155C, margin Red-Purple 64A.
*Under side*.—Base near RHS White N155C, margin Red-Purple 64A.

Color, fertile:
*Upper side*.—Near RHS Yellow-green 150B.
*Under side*.—Near R.H.S. Yellow 2D.

PEDUNCLE

Length: Range from 4 to 8 cm.
Diameter: Approximately 0.4 cm.
Angle: Approximately 25 degrees (0 degrees=straight upright).
Strength: Strong.
Color: Near R.H.S. Yellow-Green 144A.
Texture: Smooth.

PEDICEL

Length:
*Fertile*.—0.75 cm.
*Sterile*.—1.5 cm.

Diameter:
*Fertile*.—1 mm.
*Sterile*.—1.5 mm.

Angle:
*Fertile*.—Approximately 45 degrees.
*Sterile*.—0 degrees.

Strength: All pedicels sturdy.
Color:
*Fertile*.—Near RHS 64D.
*Sterile*.—Near RHS Red 54D.

Texture:
*Fertile*.—Pubescent.
*Sterile*.—Pubescent.

REPRODUCTIVE ORGANS

*Number of pistil per flower*.—Fertile: 3.
*Pistil length*.—Fertile: 1 mm.
*Stigma shape*.—Forked
*Stigma color*.—Fertile: Near RHS 64D.
*Style color*.—Fertile: Near RHS 155B.
*Style length*.—Fertile: less than 1 mm.
*Ovary color*.—Fertile: Near RHS 155B.
*Stamens*.—Fertile: 12.
*Anther shape*.—Fertile: Kidney shaped and basally attached.
*Anther size*.—Fertile: 1 mm.

*Anther color*.—Fertile: Near RHS Yellow 4D.
*Pollen color*.—Fertile: Near RHS Yellow 4D.
*Pollen quantity*.—Little.

OTHER CHARACTERISTICS

Disease and pest resistance: Neither resistance nor susceptibility to normal diseases or pests of *Hydrangea* has been observed in this variety.

Drought tolerance and cold tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.

Fruit/seed production: No fruits/seeds detected to date.

What is claimed is:

1. A new and distinct cultivar of *Hydrangea* plant named 'STMS1' as herein illustrated and described.

* * * * *